United States Patent [19]

Wang

[11] Patent Number: 4,663,277
[45] Date of Patent: * May 5, 1987

[54] VIRUS DETECTION METHOD AND MATERIALS

[75] Inventor: Chia-Gee Wang, Millwood, N.Y.

[73] Assignee: Profile Diagnostic Sciences Inc., Warrington, Pa.

[*] Notice: The portion of the term of this patent subsequent to Mar. 13, 2001 has been disclaimed.

[21] Appl. No.: 496,541

[22] Filed: May 20, 1983

[51] Int. Cl.$^4$ .................. C12Q 1/70; C12Q 1/00; G01N 53/00; G01N 33/543; G01N 33/553; G01N 33/549; G01N 33/546

[52] U.S. Cl. .................................... 435/5; 435/7; 435/4; 435/805; 435/810; 436/518; 436/523; 436/525; 436/531; 436/532; 436/533; 436/546; 436/800; 436/805; 436/808; 436/810; 436/820; 436/824; 436/825; 422/61

[58] Field of Search ............... 435/4, 5, 7, 805, 810; 436/511, 518, 523, 525, 526, 531, 532, 533, 534, 545, 546, 548, 800, 804, 805, 806, 808, 810, 820, 824, 825; 422/61

[56] References Cited

U.S. PATENT DOCUMENTS

| | | | |
|---|---|---|---|
| 3,088,875 | 5/1963 | Fisk | 436/509 |
| 3,853,987 | 12/1974 | Dreyer | 427/1 |
| 4,108,972 | 8/1978 | Dreyer | 424/1 |
| 4,219,335 | 8/1980 | Ebersole | 436/526 |
| 4,231,750 | 11/1980 | Dowben et al. | 23/230 B |
| 4,267,234 | 5/1981 | Rembaum | 436/526 |
| 4,273,756 | 6/1981 | Ling et al. | 436/518 |
| 4,297,337 | 10/1981 | Mansfield et al. | 436/526 |
| 4,331,649 | 5/1982 | Chantler et al. | 436/534 |
| 4,353,984 | 10/1982 | Yamada et al. | 435/28 |
| 4,360,358 | 11/1982 | Sharma | 435/7 |
| 4,371,624 | 2/1983 | Saxholm | 435/4 |
| 4,386,826 | 5/1984 | Wang | 436/525 |
| 4,452,773 | 6/1984 | Molday | 436/526 |
| 4,454,233 | 6/1984 | Wang | 436/525 |

FOREIGN PATENT DOCUMENTS

| | | | |
|---|---|---|---|
| 0031646 | 3/1981 | Japan | 436/511 |
| 0151357 | 11/1981 | Japan | 436/518 |
| 82/01072 | 4/1982 | PCT Int'l Appl. | 435/7 |

OTHER PUBLICATIONS

"Diagnostic Virology", Third Ed. (1982), G. D. Hsiung, Yale Univ. Press, New Haven, pp. 3-6.
"Immunology", (1981), The Upjohn Company, Kalamazoo, p. 9.

*Primary Examiner*—Thomas G. Wiseman
*Assistant Examiner*—Robin Lyn Teskin
*Attorney, Agent, or Firm*—Joseph H. Handelman

[57] ABSTRACT

Viruses are detected by means of an immunoassay method in which an extended solid phase coated with antiviral antibody is employed to bind and remove virions from a specimen by forming an immuno-complex with antigens of said virions, a mobile solid phase comprising a dispersion of microspheres coated with the antiviral antibody is used to bind said microspheres to antigens associated with said immuno-complex, and the presence of bound microspheres is detected. The detection sensitivity is amplified by the ability to more readily detect the microspheres, which may be dyed or labelled. The extended solid phase advantageously may be in the form of a dipstick which can be easily contacted with the specimen. A virus detection kit provides the extended solid phase and mobile solid phases, each coated with antiviral antibodies.

40 Claims, 5 Drawing Figures

VIRUS DETECTION METHOD AND MATERIALS

BACKGROUND OF THE INVENTION

1. Field of the Invention

The invention relates to the detection and/or the determination of viruses by an immunoassay method, to materials for such method, and to a virus detection kit.

2. Description of the Prior Art

A number of methods are available in clinical virology which can be used to detect viruses or certain viral antigens (Ag). Infectivity assays depend upon biological amplification, i.e., the ability of viruses to multiply and provide adequate amounts for observation. In vitro methods include infection of cells for plaque formation or other readily observed cytopathic effects, whereas in vivo methods require an infection which causes the death of injected animals. These infectivity assays are accurate with respect to the presence of viable virions, but they do not directly provide viral specificity, and the procedures are tedious and time con- suming.

As indicated in Diagnostic Virology, G. D. Hsiung, Third Edition (1982), Yale University Press, New Haven and London, pages 3-6, an alternative to these methods are immunoassays which depend on the detection of a specific viral Ag by an antibody (Ab) which forms an immuno-complex with the Ag. Methods such as Immunofluorescence, Enzyme Immunoassay, and Radioimmunoassay are the three most well developed assays. They measure the presence of viral Ag, which can be the capsomere proteins of the virion, the neuraminidase and haemagglutinin "spikes" of the virion or the viral nucleic acids. These assay methods are highly specific, fast and sensitive relative to infectivity assays, but viral viability must still be verified by infectivity tests. Direct observation of virions using negative staining and an electron microscope or using immunoelectromicroscopy generally does not offer sufficient sensitivity, but has advantages of being faster than the assay methods and requiring a minimum of specimen preparation. The known assay methods have a number of limitations. Enzyme Immunoassay requires use of elaborate and costly chemistry. Radioimmunoassay involves steps requiring lengthy incubation times, and the difficulty of handling radioactive materials. Immunofluorescence methods are generally less sensitive. There is accordingly a need for a more sensitive, faster and economical method for the detection of viruses.

The method of choice, therefore, depends on the nature of the specimen, the need for rapid detection and/or high sensitivity, as well as the availability of detection instruments and reagents.

U.S. Pat. No. 3,088,875 granted on May 7, 1963 to Roy T. Fisk, discloses tests for antigens or antibodies indicative of pathological conditions, employing polymeric styrene latex having particle size of 0.15 to 0.25 micron as a carrier for specific, known antibodies or antigens. The carrier is dyed, and the presence of unknown antibodies or antigens in a specimen is determined by visual observation of flocculation of the test reagent, due to formation of immune-complexes in the mixture on a glass slide.

The introduction of tracers or labels on to microscopic particles or strands of carrier material, and use of such labelled particles in immunoassays is described in U.S. Pat. No. 3,853,987 granted on Dec. 10, 1974 to William J. Dreyer, the disclosure of which is incorporated herein by reference.

In the present applicant's copending U.S. patent application Ser. Nos. 313,711, now allowed U.S. Pat. No. 4,436,826, filed on Oct. 21, 1981 and 331,859, now allowed U.S. Pat. No. 4,454,233, filed on Dec. 17, 1981, the disclosures of both of which are incorporated herein by reference, antibody or antigen coupled microspheres having isolated tagging or labelling materials therein are disclosed for use in immunoassays. These applications also disclose use of a solid phase material which is employed for the separation of bound and free microspheres. A number of detection methods for the labelled microspheres are disclosed such as X-ray fluorescence.

SUMMARY OF THE INVENTION

The present invention provides a method for detection of viruses in a specimen, wherein said specimen, treated to remove undesired components, is contacted with an extended solid phase having conjugated thereon antiviral antibody ($Ab_v$) to form immuno-complexes with antigens characteristic of the viruses to be detected; the extended solid phase is separated from the specimen; said separated extended solid phase is contacted with a mobile solid phase consisting of dispersed microspheres having conjugated thereto said $Ab_v$ to bind said microspheres to said immuno-complexes; the extended solid phase is separated from said mobile solid phase; and the presence of microspheres bound to said extended solid phase is detected, whereby the presence of viruses in said specimen is detected or determined.

Also, the invention provides a virus detection kit which comprises as individual components: (a) an extended solid phase having conjugated thereon antiviral antibody ($Ab_v$) capable of forming immuno-complexes with antigens characteristic of the viruses to be detected; and (b) a mobile solid phase consisting of dispersed microspheres having said $Ab_v$ conjugated thereto.

In accordance with the present invention, a new method of immunoassay is disclosed which involves solid phase amplification and is particularly suitable for virus detection. The method of the invention uses an Ab-conjugated mobile solid phase which when bound to Ag can be measured by simple instruments with very high sensitivity.

A specimen which may comprise viruses of types to be detected is exposed to an extended solid phase component which is coated at least in one location with $Ab_v$ which will form complexes with the antigens of the viruses to be detected. The extended solid phase is separated from the specimen, such as by washing the specimen off the extended solid phase, and the separated extended solid phase is then contacted with a mobile solid phase of dispersed microspheres including the same $Ab_v$ thereon. If immuno-complexes of antigens of viruses to be detected ("target" viruses) have formed on the extended solid phase, the microspheres will be bound to such complexes.

The unbound microspheres of the mobile solid phase then are removed, such as by washing, and the extended solid phase is examined to determine the presence of microspheres bound to the extended solid phase. These may be visually detected in some cases, for example when the microspheres have been initially stained or dyed. Microscopic examination may be employed. The use of tracers or labels for the microspheres enables the use of other detection methods.

By this means, the presence or absence of bound microspheres enables detection of the presence or absence of the target viruses, and an evaluation of the quantity of bound microspheres enables determination of the quantity of viruses in the specimen, for example by comparison with standard results for the assay of known samples.

DESCRIPTION OF THE PREFERRED EMBODIMENTS

The extended solid phase used in the present invention may be employed in a variety of forms or structures, it only being necessary for the solid phase to have a location where $Ab_v$ is conjugated thereon, and for the solid phase with said $Ab_v$ to be formed so as to enable contacting with the specimen and other materials used in the method of the invention. Thus, the extended solid phase is best formed in a way which enables simple manipulation for easy contact with the specimen and other reagents. For this purpose, the extended solid phase may form at least part of a dipstick, syringe, tube or container. The specimen and other reagents can be drawn in and ejected from a syringe, caused to flow through a tube, or deposited in a container such as a test tube shaped container. In such devices, the extended solid phase can form the whole of the device, or part of it, where, in the case of a syringe, tube or container, the part formed of the extended solid phase will at least be exposed at the inside of the device to permit contact with specimen and reagents. Preferably, $Ab_v$ is concentrated at one location of the extended phase, to be exposed to the specimen.

The most preferred form of the extended solid phase is a dipstick. In such a dipstick, it is further preferred that the extended solid phase should be included at at least one end, and that the $Ab_v$ conjugated on the extended solid phase should be concentrated at the end of the dipstick. The extended solid phase can however comprise the entire dipstick, with the $Ab_v$ concentrated at one end, or in more than one location.

Figure 1:
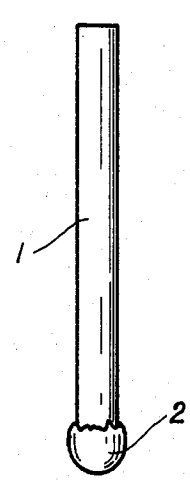
FIG. 1 illustrates schematically an elevation of an embodiment of the extended solid phase of the invention in the form of a dipstick.
Figure 2:
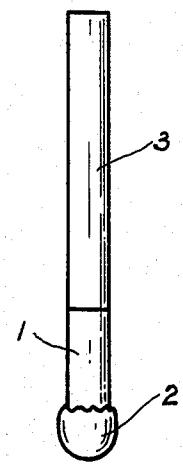
FIG. 2 illustrates schematically an elevation of another embodiment of the dipstick.

In FIG. 1 a dipstick is shown, which is entirely formed from the extended solid phase 1, at one end of which has been conjugated a coating 2 of $Ab_v$. FIG. 2 illustrates another dipstick embodiment made of the extended solid phase 1 one end of which is adhered to a body portion 3. A coating 2 of $Ab_v$ is conjugated to the extended solid phase. In another embodiment shown in FIG. 3, the extended solid phase entirely forms a tubular container 4, into which a specimen can be placed. Coatings 2 of $Ab_v$ are located near the bottom of the container 4, and are concentrated in two locations.

The extended solid phase is composed of any material onto which the desired $Ab_v$ can be effectively bound. For covalent binding with Ab protein, the solid phase material can be chosen to contain a functional carboxyl surface, with use of a water-soluble carbodiimide as a conjugation reagent. A preferred material is acrylic resin, which has a carboxylated surface that enables binding the desired $Ab_v$ by conjugation. For materials with amino surface groups, reactive carboxyl intermediates can be prepared by reacting with succinic anhydride. A variety of inorganic supports, typically glass, can also be prepared for covalent coupling with $Ab_v$. Reference is made, for example, to "Enzymology, A Series of Textbooks and Monographs," Vol. 1, Chapter 1, 1975, the disclosure of which is incorporated herein by reference.

It is necessary to choose extended solid phase materials which bind $Ab_v$ without causing serious interference with the assay steps. Hydrophobic polystyrene latex, for example, tends to stick non-specifically to many surfaces and molecules, and would not be a proper choice to carry specific immunoreagents. It can, however, be used as a deleting element in an affinity column for pretreatment of the specimen to remove undesired elements such as rheumatoid factor, etc. Hydrophilic polymeric latex, on the other hand, does not bind non-specifically and can provide functional groups to covalently conjugate the Ab protein.

The presence of non-specific agglutinators in a tissue specimen, particularly those coupled to immunoglobulins, can result in error by causing the binding of mobile microspheres to the extended solid phase even in the absence of specific Ag. Repeated washes during the assay would reduce the non-specific binding, but removal of the non-specific agglutinators is necessary in order to avoid such undesired binding. A simple polystyrene latex surface, for example, can passively delete some of the agglutinators, whereas an Ig G-coated surface provides a better affinity.

For convenience in the following description, the extended solid phase generally will be referred to as the preferred dipstick, although other forms may be used as explained above.

A typical viral particle has an envelope of many, usually over one hundred, identical Ag proteins or protein sets. The proteins provide very strong binding with specific Ab and form multiple conjugates or immune complexes. Highly specific Ab in monoclonal form has become available, either produced by hybridoma for the selected monoclonal mouse Ab, or by the human B-lymphocytes transformed by the Epstein-Barr virus for the human IgM. When properly chosen, these monoclonal antibodies can provide consistant and reproducible binding with virions. With a proper supply of specific Ab, the present direct binding immunoassay, in contradistinction with competitive binding immunoassay practiced in radioimmunoassay, can be a reliable and very rapid procedure since the incubation time for a kinematic equilibrium needed in competitive binding assays is not presently required.

In accordance with the method of the present invention, antiviral antibody $Ab_v$, either from the usual Ig fraction of the antisera or from monoclonal antibodies, is conjugated respectively with a solid phase dip stick as well as with a mobile solid phase, or the so called "monodispersed", microspheres. The functions of the dip stick are for the handling and the separation of bound from free antigens, whereas that of the mobile microspheres are for the detection of the formed immuno-complexes. Coupling techniques between the Ab protein and various solid phase materials are well developed (see, for example, the above-mentioned W. J. Dreyer, U.S. Pat. No. 3,853,987).

The method of the present invention results in the following coupling:

Dip Stick+$Ab_v$+Viral Ag+$Ab_v$+Microsphere.

Figure 3:
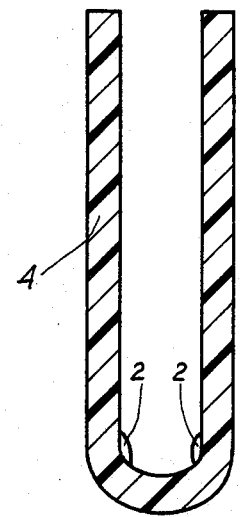
FIG. 3 illustrates schematically a sectional elevation of the extended solid phase of the invention in the form of a tubular container.

The amount of Ab required for covalent binding, however, can be a thousand times that of passive absorption to a plastic such as polyvinyl chloride and the economics of using such an amount of highly specific $Ab_v$ can be prohibitive. An alternative way, retaining some strength of the covalent binding as well as the specificity of $Ab_v$, is to bridge the $Ab_v$ and the solid phase with an antispecies antibody $Ab_s$, targeted against the $F_c$ portion of immunoglobulin $Ab_v$. The $F_c$ portion is shown in FIG. 3 on page 9 of "Immunology" (1981), The Upjohn Company, Kalamazoo, Mich. That is, inexpensive $Ab_s$, is first covalently bound to the solid phase, and the bound $Ab_s$ attracts the species-specific $F_c$ portion of $Ab_v$, leaving the functional epitope of $Ab_v$ unaltered with regard to the viral Ag. Bridged with $Ab_s$, the immunoassay of the present invention brings about the following coupling:

Dip Stick+$Ab_s$+$Ab_v$+Viral Ag+$Ab_v$+$Ab_s$+Microsphere.

In the direct binding assay of the present invention, the couplings between the dipstick and $Ab_v$ as well as the Microspheres and $Ab_v$ are prepared in advance, and elements of non-specific agglutination in the fluid specimen are removed or deactivated for pretreatment prior to the direct binding assaying as mentioned above. The assaying procedure of the invention is therefore simplified to the following steps:
(1) Insert the dipstick into the pretreated specimen.
(2) Wash.
(3) Insert the dipstick into the $Ab_v$ coated microsphere dispersion.
(4) Wash.
(5) Detect the microspheres on the dipstick.

In order to use a minimal amount of wet chemistry, the present detection of attached microspheres on a dip stick is made independent of the immune chemistry. By concentration of the $Ab_v$ at one end of the dipstick, the bound microspheres are concentrated at one location, which simplifies detection. The microspheres can include dye or fluorescent compounds for direct visual observation, or have metal elements or iron oxide doped or entrapped within in order to provide X-ray fluorescent or electromagnetic signals. Enzymatic amplification can also be designed into the microspheres, but it is not preferred in the present invention, because the enzymatic reaction must necessarily involve additional wet chemistry.

Conjugated with the microspheres, each Ag becomes coupled to, and therefore amplified with a solid phase material of $10^7$ or more atoms for signal detection. With use of a good fluorescent microscope, the fluorescent microspheres can be seen at a size as small as 0.1 $\mu$m, clearly and without fading. In other words, the immune complexes can be counted individually as represented by the coupled mobile solid phase. Without using a microscope, a concentration of about one thousand fluorescent microspheres can be seen at the tip of the dipstick by the observer's unaided eyes under a UV lamp and with a dark field background. Colored microspheres of the same small size (0.1 $\mu$m) would require a few thousands in order to be directly visible. It is notable that in an infectivity assay or radioimmunoassay, the limiting sensitivity is about $10^6$ virions or Ag, which is several orders of magnitude less sensitive than the above indicated sensitivity of the present assay. Moreover, in the present assay no detection instrument or additional wet chemistry is required for the indicated visual sensitivity.

Detection by X-ray fluorescence or by magnetic force enables minimal handling and avoids subjective judgement. In the above-mentioned copending U.S. patent application Ser. Nos. 313,711, now U.S. Pat. No. 4,436,826, and 331,859, now allowed U.S. Pat. No. 4,454,233, the doping of metal elements in microspheres and methods of their detection are disclosed, and can be employed for the present detection step.

Figure 4:
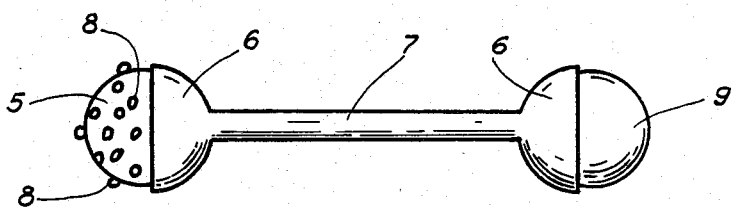
FIG. 4 is a schematic elevation of the extended solid phase of the invention in the form of a sphere for use with magnetically labelled microspheres.
Figure 5:
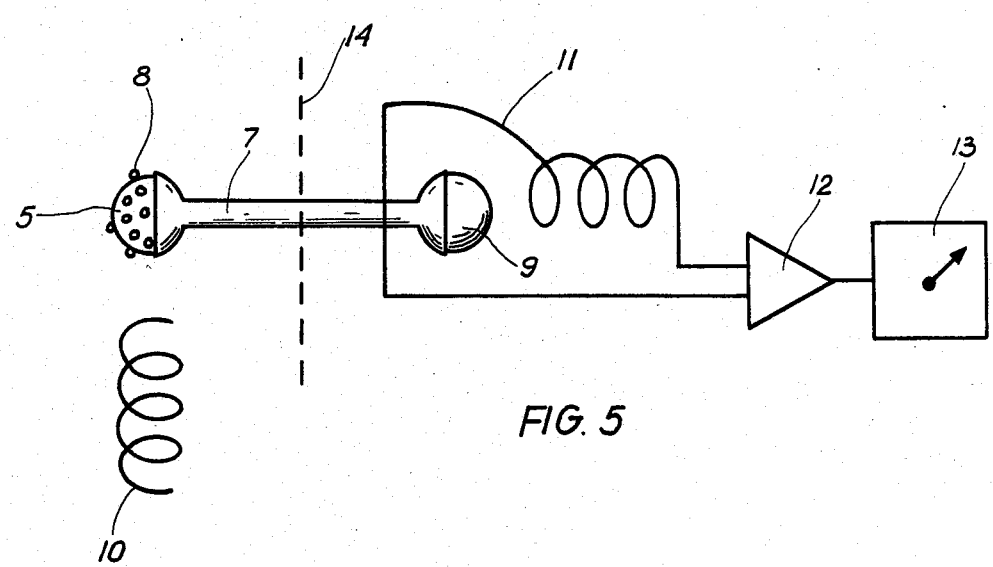
FIG. 5 is a schematic representation of a detection device for use with the extended solid phase of FIG. 4.

Magnetic microspheres can be made in polyglutaraldehyde material. The iron oxide entrapped particles should be demagnetized in order to have the Ab protein properly coated and their size selected without interference from spontaneous agglutination. A membrane filter with well defined pore size can eliminate, and thereby select the desired particle sizes without centrifuging. In the method of the present invention, the detection of magnetic microspheres is done similarly to that of a Faraday magnetometer where an intense magnetic field changes the weight of the magnetic particles. As shown in FIG. 4, the dipstick for this embodiment has a non-magnetic sphere or ball 5 for assaying. The ball 5 is first conjugated with $Ab_v$ and in the assay would be coated with the mobile, $Ab_v$ coupled magnetic particles 8 in the presence of specific Ag. Before the assay, ball 5 is fitted into one of two sockets 6 connected by bridge member 7. After assaying, non-magnetic ball 5 is connected by bridge 7 to a second ball 9 of the same size, which is magnetic and is inserted into the other socket 6. The two balls and the bridge 7 form a dumb bell configuration, and would vibrate if either end is forced to oscillate, particularly if the oscillating frequency strikes a resonance with the natural frequency of the dumb bell. As illustrated in FIG. 5, operating like the needle of a record player, the dumb bell's assayed ball 5 which may be coated with magnetic microspheres 8 is placed with a driving coil 10 whereas the second, highly magnetic ball 9 is enclosed in a pickup coil 11. The pickup coil 11 emits signals to be amplified by an audio amplifier 12 for display in meter 13. A high mu shield 14 separates the two balls. It is known that a sensitive vibrating reed synchronized by a stroboscope can detect an iron particle at about one $\mu$m in size without using superconducting designs (H. Zijlstra, Rev. Sci. Instruments, 41, 1241; 1970). A vibrating reed coupled with an unknown amount of magnetic material cannot aim to vibrate at a set resonant frequency, but in the present dumb bell embodiment, the masses of the two balls remain essentially constant, as therefore also does the dumb bell's natural frequency. Accelerating at near the resonant frequency by a driving coil coupled to the assayed sphere, this very simple system can measure an iron conjugation at about 10 $\mu$m in total size. Such an amount of magnetic material is minimally required for one "bit" of signal in a sensitive magnetic tape. Using magnetic particles at about 0.4 $\mu$m each, a viral sensitivity of $10^3$–$10^4$ virions appears possible in the present embodiment.

Preferably, the present method employs a direct binding assay instead of a competitive binding assay where a dynamic equilibrium necessitates lengthy incubation. The disclosed method can, of course, be employed in a competitive protein binding assay as well. The roles of the immune analytes Ab and Ag can also be interchanged, still making use of the immobilized solid phase for the signal amplification. Binding of Ab or various Ag molecules to the solid phase matter is well known, in passive absorption as well as in covalent coupling.

In the immunoassay of the present invention, the viral Ag, which appears in high multiplicity, is used as a bridge to connect the mobile and the immobilized solid phases. This connection can obviously be served by various other Ag with multiple Ab binding sites. In cases of certain Ag without repetitive binding sites which cannot specifically connect more than one monoclonal Ab, polyvalent Ab must be used instead.

With use of detection equipment providing multiple signal channels, such as the X-ray lines where each may correspond to the X-ray fluorescence of a particular metal element, the method of the invention can also be designed to assay several analytes in a single procedure where each analyte is represented by a particular element corresponding to a particular X-ray line.

Detection of different types of viruses can be done in accordance with the invention by conjugating a plurality of different $Ab_v$ proteins capable of forming complexes with corresponding antigens of different viruses, respectively to the extended solid phase and to the mobile solid phase. The visual observation or other detection of any bound microspheres following the assay indicates that one or more of the different viruses is present in the specimen, and this assay, if positive, can be followed by assays for individual viruses of the different ones which were tested for simultaneously.

In another embodiment, the different viruses can be both simultaneously and individually detected. For such a test, the different $Ab_v$ proteins corresponding to the antigens of a plurality of different types of viruses are conjugated to microspheres which are correspondingly labelled with different metal elements. When more than one type of the differently labelled microspheres are bound to the extended solid phase in the assay of the invention, they may be separately and simultaneously detected by X-ray fluorescence of the different metal element labels. In this way, the presence of corresponding individual types of viruses in the specimen are simultaneously and separately detected.

The extended solid phase and the dispersed microspheres which are conjugated with $Ab_v$, prepared as described above as individual components useful for the assay method of the invention, can be provided in the form of a virus detection kit comprising such components. Different kits may be provided, which differ as to the $Ab_v$ coatings, and thus as to the viruses to be detected.

Such a kit may further include as an individual component, a latex solid phase for removing non-specific agglutinators from a specimen prior to the assay. The preferred latex for this purpose is polystyrene coated with gamma immunoglobulin.

The extended solid phase and mobile solid phase components of the kit of the invention may be provided with $Ab_v$ bound to $Ab_s$ as disclosed above. Also as disclosed above, the microsphere component may be labelled, and the extended solid phase can take the form of part or all of a dipstick, syringe, tube or container, coated with $Ab_v$ in at least one location, as disclosed.

Furthermore, the extended solid phase component may be provided with a plurality of different $Ab_v$ proteins capable of forming complexes with corresponding antigens of different types of viruses. When it is so provided, the individual mobile solid phase component can be provided either to have the same plurality of $Ab_v$ conjugated to each of the microspheres thereof, or a mixture of different types of microspheres can be provided, each type having conjugated thereto a different $Ab_v$ protein of said plurality; or in a further variation, the mobile solid phase component can be provided in the form of separate batches of microspheres, each batch having conjugated thereto a different $Ab_v$ protein of said plurality.

Viral Ag to be assayed can be the Herpes Simplex Viruses in various organs, particularly from the cervical PAP smears, from glycoprotein in cerebrospinal fluid; the Cytomegaloviruses (CMV) in urine, kidney, lung and brain; the Varicella-Zoster viruses in the brain; the Cox-Sackie B group viruses in the heart; the Measles viruses in lymph node and lung; the Respiratory syncytial viruses in nasal secretions and in the lung; the Hepatitis B viruses in serum; the Hepatitis A viruses in stool, etc. Since the clinical goal of viral assay is often the absence of the analyte of interest, and not its amount, several viral analytes can therefore be combined into a single test. For example, from a lung tissue, the Ab conjugated microspheres can include the tests for the Herpes viruses, the Cytomegaloviruses, and the Respiratory syncytial viruses. Only in the presence of a positive result, should the test proceed further for a specific and quantitative identification.

In the following description, materials and reagents were mostly obtained from Polysciences, Warrington, PA. 18976. Membrane filters and cartridge holders were obtained from Bio-Rad Labs., Richmond, Calif. 84804.

EXAMPLE 1

Coupling of Ab Protein to the Solid Phase Matter

Polymethyl methacrylate latex (Nature 249, 81; 1974) is used to form monodispersed microspheres with a functional carboxylated surface, and the conjugation reagent 1-ethyl-3-(3-dimethyl-aminopropyl) carbodiimide, or ECDI, (latex microspheres and ECDI from Polysciences; see "methods in Enzymology", 70, 151; 1980) readily couples the carboxylated surface with the amino group of the protein, usually the lysyl or the alanyl residues:

(i) 10 $\mu$l of 0.09 $\mu$m carboxylated beads ($5 \times 10^{11}$ beads) are added to 100 $\mu$l of saline, (ii) to 10 $\mu$l of the bead-saline suspension, add 90 $\mu$l of $Ab_s$ (Rabbit anti-Goat) at the highest concentration available, (iii) ECDI at 10 mg/100 $\mu$l cold saline (4° C.) is prepared and immediately mixed with the bead-saline-Ab suspension and the reaction is permitted to continue at 4° C. for one hour with mild agitation of the mixture all the while, and with the pH kept at between 7.4–7.9 all the time, (iv) coated beads are recovered with a membrane filter (Unipore from Bio-Rad) after washes and suspended in 10 ml saline ($5 \times 10^{10}$ beads/ml), (v) 10 μl of Goat $Ab_v$ (anti-cytomegalovirus, Polysciences) is added to the $Ab_s$ coated beads at 4° C. and mildly agitated for one hour. The coated beads are again washed and recovered with a filter, and suspended in 10 ml saline. The beads are ready for assay.

A dipstick of the same material as above for the microspheres is coated at the tip with the same antibodies as above.

EXAMPLE 2

Removal of Non-Specific Agglutinator 10 ml polystrene tubes are incubated with 2.5 ml of 0.1% glutaraldehyde in 0.1 M carbonate buffer, pH 9.0 for 3 hours at an elevated temperature (50°-60° C.). The tubes are cooled and washed thoroughly, and 2 ml of human IgG at 100 μg/ml are added and incubated overnight at 4° C. The tubes are washed with phosphate-buffered saline (PBS) at pH 7.2 and the bound IgG is fixed by 2.5 ml of 0.05% glutaraldehyde in PBS for 1 hour at 25° C. Finally, the tubes are washed thoroughly and with the residue free aldehyde inactivated by 3 ml of 1% glycine in PBS. About 1.5% of the starting IgG remains bound to the tube surface.

A tissue specimen is lysed and homogenized to expose the virions and is incubated in the coated-tube for 1 hour at 25° C. in order to remove the undesired agglutinators. Incubating in a second tube is done when necessary to thoroughly remove the agglutinators. The coated-tubes should not be reused for sensitive assays where the specimen contamination may be of concern.

EXAMPLE 3

Demagnetization of Micromagnetic Spheres

Iron containing microspheres are made of polyglutaraldehyde matrix (J. of Immunological Methods, 28, 341; 1979, and Polysciences.) The particles, however, are not provided with uniform sizes, and they tend to agglutinate spontaneously. The magnetic agglutination cannot be separated by simple sonification (ultrasound vibration). Prior to the coating of Ab, the magnetic microspheres must be demagnetized and their sizes sorted (Unipore filter from Bio-Rad.) During various stages of coating, storage, and assaying, the spheres must avoid the presence of magnetic field or magnetized material. Demagnetizing of the microspheres consists of the following steps:

The iron containing microspheres are placed in a gel, or in a frozen state to remain motionless. An oscillating magnetic field, usually with the household frequency of 60 Hz, is applied to the gel to magnetize the particles to the maximum, reversing back and forth at 60 Hz, and the field strength is reduced by spatial distance to a zero level as the gel physically leaves the field. The gel is sonicated at $10^5$ Hz while returning to a liquid state and is placed in a high μ shield and in a gel state for storage in order to avoid the undesired spontaneous agglutination.

EXAMPLE 4

Display of Magnetic Signals

A sphere of non-magnetic material having a size of 40 μm is first coated with the desired $Ab_v$. This sphere is fitted into one of the two sockets of a bridge as shown in FIG. 4. The socket without a sphere is to be filled by inserting a highly magnetic sphere, also having a size of 40 μm, after the immunoassay. The second sphere does not participate in assaying procedures, and its sole function is to enhance the presence of the immunologically coated magnetic material of the first sphere.

The non-magnetic sphere, coated with $Ab_v$ and held by the bridge, may fish out the $Ab_v$ coated magnetic microspheres in the presence of specific Ag and become slightly magnetic. The second highly magnetic sphere is inserted into the bridge after the immunoassay. A driving alternating magnetic force at a frequency near the resonant frequency of the dumb bell configuration is tuned at the first coated sphere, whereas a pickup coil surrounding the second magnetic sphere senses its vibration, which is amplified and displayed on a meter.

EXAMPLE 5

Assaying Procedure

The dipstick and microspheres prepared as in Example 1 and 2 are used.

In Example 1 the tip of the dipstick and the mobile fluorescent microspheres are each coated with certain $Ab_v$ using $Ab_s$ as bridging element, and in Example 2, non-specific agglutinators, such as the IgM class of rheumatoid factors, are removed from the serum specimen. The assaying procedure for CMV is simplified to the following steps.

A dipstick of anti-CMV Ab coated at its surface tip is inserted into a 0.5 ml serum specimen treated for the removal of non-specific agglutinators, in a sodium phosphate buffer, pH 7.0, for 10 minutes at 4° C. with mild agitation. The dip stick is washed twice and inserted into 0.5 ml of anti-CMV Ab coated microspheres with 1/1000 dilution, for 5 minutes at 4° C. with mild agitation, and again washed twice. The presence of fluorescent microspheres at the coated area, the tip, of the dipstick is detected by examining visually with UV illumination against a dark field background. As few as several thousand CMV virions in 0.5 ml serum are detected in this procedure.

I claim:

1. A method for detection of viruses in a specimen comprising;
    treating the specimen to remove undesired components;
    contacting the specimen with a solid phase support having conjugated thereto antiviral antibody ($Ab_v$) which is capable of forming immuno-complexes with antigens characteristic of the viruses to be detected;
    separating the solid phase support from the specimen;
    contacting said separated solid phase support with a mobile solid phase consisting of dispersed microspheres smaller than 0.1 μm, said microspheres being labelled with metal elements and having conjugated thereto said $Ab_v$ which enables the binding of said microspheres to said immuno-complexes;
    separating the unbound mobile solid phase from the solid phase support; and
    measuring the presence of microspheres bound to said solid phase support by X-ray fluorescence, thereby detecting or determining the presence of viruses in said specimen.

2. A method according to claim 1, wherein before contacting with the solid phase support, the specimen is contacted with a polystyrene latex surface coated with gamma immunoglobulin to remove non-specific agglutinators.

3. A method according to claim 1, wherein the $Ab_v$ is monoclonal.

4. A method according to claim 1, wherein the solid phase support is both separated from the specimen and also separated from the mobile solid phase by washing.

5. A method according to claim 1, wherein antispecies antibody ($Ab_s$) is covalently bound to the solid phase support and is bound to the mobile solid phase, and $Ab_v$ which forms an immuno-complex with said $Ab_s$ is coupled therewith, whereby there is conjugated to said solid phase support and to said mobile solid phase $Ab_v$ which is capable of forming immuno-complexes with antigens of viruses to be detected.

6. A method according to claim 5, wherein the $Ab_v$ is monoclonal.

7. A method according to claim 1, wherein the solid phase support forms at least part of a dipstick, syringe, tube or container.

8. A method according to claim 1, wherein the solid phase support forms at least part of a dipstick, said solid phase support being included at least at an end of said dipstick.

9. A method according to claim 8, wherein the $Ab_v$ conjugated on the solid phase support is concentrated at an end of the dipstick.

10. A method according to claim 7, wherein the solid phase support comprises an acrylic resin, or comprises an inorganic material treated for covalent coupling with antibody protein.

11. A method according to claim 1, wherein a plurality of different $Ab_v$ proteins capable of forming complexes with corresponding antigens of different types of viruses are conjugated to the solid phase support and are conjugated to the mobile solid phase, whereby the presence of one or more of a plurality of different types of viruses in the specimen is detected.

12. A virus detection kit, which comprises as individual components:
(a) a solid phase support having conjugated thereon antiviral antibody ($Ab_v$) capable of forming immuno-complexes with antigens characteristic of the viruses to be detected, said antiviral antibody consisting of a plurality of different $Ab_v$ proteins capable of forming complexes with corresponding antigens of different types of viruses; and
(b) a mobile solid phase consisting of dispersed microspheres smaller than 0.1 μm, said microspheres being labelled with a plurality of metal elements which can be detected by X-ray fluorescence and having said different $Ab_v$ proteins conjugated thereto, said mobile solid phase being either in the form of a mixture of different types of microspheres, each type having conjugated thereto a different $Ab_v$ protein, the different $Ab_v$ proteins being capable of forming complexes with corresponding antigens of different viruses, or in the form of separate batches of microspheres, each batch having conjugated thereto a different $Ab_v$ protein, said different $Ab_v$ proteins being capable of forming complexes with corresponding antigens of different viruses; wherein the components are present in amounts sufficient to perform the virus detection assay.

13. A kit according to claim 12, further including as an individual component:
(c) a latex solid phase capable of removing non-specific agglutinators from a specimen.

14. A kit according to claim 13, wherein said latex is polystyrene coated with gamma immuno-globulin.

15. A kit according to claim 12, wherein the solid phase support component (a) and the mobile solid phase component (b) each have antispecies antibody ($Ab_s$) covalently bound thereto, and $Ab_v$ which forms an immuno-complex with said $Ab_s$ coupled therewith, whereby said solid phase support component (a) and said mobile solid phase component (b) each have conjugated thereto $Ab_v$ which is capable of forming immuno-complexes with antigens of viruses to be detected.

16. A kit according to claim 12, wherein the solid phase support component (a) forms at least part of a dipstick, syringe, tube or container.

17. A kit according to claim 12, wherein the solid phase support forms at least part of a dipstick, said solid phase support being included at least at an end of said dipstick.

18. A kit according to claim 17, wherein the $Ab_v$ conjugated on the solid phase support is concentrated at an end of the dipstick.

19. A kit according to claim 16, wherein the solid phase support comprises an acrylic resin, or comprises an inorganic material treated for covalent coupling with antibody protein.

20. A method for detection of proteins in a specimen comprising;
treating the specimen to remove undesired components;
contacting the specimen with a solid phase support having conjugated thereto antiprotein antibody (Ab) which is capable of forming immuno-complexes with antigens characteristic of the proteins to be detected;
separating the solid phase support from the specimen;
contacting said separated solid phase support with a mobile solid phase consisting of dispersed microspheres, smaller than 0.1 μm, said microspheres being labelled with metal elements and having conjugated thereto said Ab which enables the binding of said microspheres to said immuno-complexes;
separating the unbound mobile solid phase from the solid phase support; and measuring the presence of microspheres bound to said solid phase support by X-ray fluorescence, thereby detecting or determining the presence of proteins in said specimen.

21. A method according to claim 20, wherein before contacting the solid phase support, the specimen is contacted with a polystyrene latex surface coated with gamma immunoglobulin to remove non-specific agglutinators.

22. A method according to claim 20, wherein the Ab is monoclonal.

23. A method according to claim 20, wherein the solid phase support is both separated from the specimen and also separated from the mobile solid phase by washing.

24. A method according to claim 20, wherein antispecies antibody ($Ab_s$) is covalently bound to the solid phase support and to the mobile solid phase, and Ab which forms an immuno-complex with said $Ab_s$ is coupled therewith, whereby there is conjugated to said solid phase support and to said mobile solid phase Ab which is capable of forming immuno-complexes with antigens of proteins to be detected.

25. A method according to claim 24, wherein the Ab is monoclonal.

26. A method according to claim 20, wherein the solid phase support forms at least part of a dipstick, syringe, tube or container.

27. A method according to claim 20, wherein the solid phase support forms at least part of a dipstick, said solid phase support being included at least at an end of said dipstick.

28. A method according to claim 27, wherein the Ab conjugated on the solid phase suport is concentrated at an end of the dipstick.

29. A method according to claim 26, wherein the solid phase support comprises an acrylic resin, or comprises an inorganic material treated for covalent coupling with antibody protein.

30. A method according to claim 20, wherein a plurality of different Ab proteins capable of forming complexes with corresponding antigens of different types of proteins are conjugated to the solid phase support and are conjugated to the mobile solid phase, whereby the presence of one or more of a plurality of different types of proteins in the specimen is detected.

31. A protein detection kit, which comprises as individual components:
(a) a solid phase support having conjugated thereon antiprotein antibody (Ab) capable of forming immuno-complexes with antigens characteristic of the proteins to be detected, said antiprotein antibody consisting of a plurality of different Ab proteins capable of forming complexes with corresponding antigens of different types of proteins; and
(b) a mobile solid phase consisting of dispersed microspheres less than 0.1 $\mu$m, said microspheres being labelled with a plurality of metal elements which can be detected by X-ray fluorescence and having said different Ab proteins conjugated thereto, said mobile solid phase being either in the form of a mixture of different types of microspheres, each type having conjugated thereto a different Ab protein, the different Ab proteins being capable of forming complexes with corresponding antigens of different proteins, or in the form of separate batches of microspheres, each batch having conjugated thereto a different Ab protein, said different Ab proteins being capable of forming complexes with corresponding antigens of different proteins wherein the components are present in amounts sufficient to perform the protein detection assay.

32. A kit according to claim 31, further including as an individual component:
(c) a latex solid phase capable of removing nonspecific agglutinators from a specimen.

33. A kit according to claim 32, wherein said latex is polystyrene coated with gamma immuno-globulin.

34. A kit according to claim 31, wherein the solid phase support component (a) and the mobile solid phase component (b) each have antispecies antibody ($Ab_s$) covalently bound thereto, and Ab which forms an immuno-complex with said $Ab_s$ coupled therewith, whereby said solid phase support component (a) and said mobile solid phase component (b) each have conjugated thereto Ab which is capable of forming immunocomplex with antIgens of proteins to be detected.

35. A kit according to claim 31, wherein the solid phase support component (a) forms at least part of a dipstick, syring, tube or container.

36. A kit according to claim 31 wherein the solid phase support forms at least part of a dipstick, said solid phase support being included at least at an end of said dipstick.

37. A kit according to claim 36, wherein the Ab conjugated on the solid phase support is concentrated at an end of the dipstick.

38. A kit according to claim 35, wherein the solid phase support comprises an acrylic resin, or comprises an inorganic material treated for covalent coupling with antibody proteins.

39. A method for detection of viruses in a specimen comprising:
treating the specimen to remove undesired components;
contacting the specimen with a solid phase support having conjugated thereto antiviral antibody (Ab) which is capable fo forming immuno-complexes with antigens characteristic of the viruses to be detected; separating the solid phase support from the specimen; contacting said separated solid phase support with a mobile solid phase consisting of dispersed microspheres, said microspheres being labelled with metal elements and having conjugated thereto said $Ab_v$ which enables the binding of said microspheres to said immuno-complexes, and wherein said $Ab_v$ conjugated to the solid phase suport and conjugated to the mobile solid phase consists of a plurality of different $Ab_v$ proteins which are capable of forming complexes with the corresponding antigens of different types of viruses, and the different $Ab_v$ proteins conjugated to the mobile solid phase are conjugated to microspheres which are correspondingly labelled with different metal elements, thereby forming a plurality of differently labelled types of microspheres, said differently labelled types of microspheres being bound to immuno-complexes of corresponding viral antigens on the solid phase support, said immunocomplexes having been formed respectively from the plurality of different $Ab_v$ proteins conjugated to the solid phase support and corresponding antigens of different types of viruses present in the specimen; separating the unbound mobile solid phase from the solid phase support; and measuring the presence of microspheres bound to said solid phase support by X-ray fluorescence, with the diferently labelled types of microsphees being separately detected by X-ray fluorescence of the different metal element labels thereby simultaneously and separately determining the presence of corresponding individual types of viruses in the specimen.

40. A method for detection of proteins in a specimen comprising;
treating the specimen to remove undesired components;
contacting the specimen with a solid phase support having conjugated thereto antiprotein antibody (Ab) which is capable of forming immuno-complexes with antigens characteristic of the proteins to be detected;
separating the solid phase suport from the specimen;
contacting said separated solid phase support with a mobile solid phase consisting of dispersed microspheres, said microspheres being labelled with metal elements and having conjugated thereto said Ab which enables the binding of said microspheres to said immunocomplexes; and wherein said Ab conjugated to the solid phase support and conjugated to the mobile solid phase consists of a plurality of different Ab proteins which are capable of forming complexes with corresponding antigens of different types of proteins, and the different Ab proteins conjugated to the mobile solid phase are conjugated to microspheres which are correspondingly labelled with different metal elements, thereby forming a plurality of differently labelled types of microspheres being bound to immuno-complexes having been formed respectively from the plurality of different Ab proteins conjugated to the solid phase support and corresponding antigens of different types of proteins present in the specimen;

separating the unbound mobile solid phase from the solid phase support; and measuring the presence of microspheres bound to said solid phase support by X-ray fluorescence with the differently labelled types of microspheres being separately detected by X-ray fluorescence of the different metal element labels thereby simultaneously and separately determining the presence of corresponding individual types of proteins in the specimen.

* * * * *

UNITED STATES PATENT AND TRADEMARK OFFICE
CERTIFICATE OF CORRECTION

PATENT NO. : 4,663,277

DATED : May 5, 1987

INVENTOR(S) : Chia-Gee Wang

It is certified that error appears in the above-identified patent and that said Letters Patent is hereby corrected as shown below:

On the Title page, item [56], right column, the 2nd listed document reads "4,386,826   5/1984 Wang" and should read -- 4,436,826   3/1984 Wang --

Signed and Sealed this

First Day of September, 1987

Attest:

DONALD J. QUIGG

Attesting Officer

Commissioner of Patents and Trademarks